(12) United States Patent
Potapov et al.

(10) Patent No.: US 11,213,241 B2
(45) Date of Patent: Jan. 4, 2022

(54) APPARATUS AND A METHOD FOR QT CORRECTION

(71) Applicant: Tampere University Foundation sr, Tampereen Yliopisto (FI)

(72) Inventors: Ilya Potapov, Tampere (FI); Esa Räsänen, Tampere (FI); Katriina Aalto-Setälä, Tampere (FI)

(*) Notice: Subject to any disclaimer, the term of this patent is extended or adjusted under 35 U.S.C. 154(b) by 0 days.

(21) Appl. No.: 17/370,660

(22) Filed: Jul. 8, 2021

(65) Prior Publication Data

US 2021/0330237 A1    Oct. 28, 2021

Related U.S. Application Data

(63) Continuation of application No. PCT/FI2020/050099, filed on Feb. 18, 2020.

(30) Foreign Application Priority Data

Mar. 22, 2019 (FI) ........................................ 20195214

(51) Int. Cl.
| | |
|---|---|
| A61B 5/00 | (2006.01) |
| A61B 5/36 | (2021.01) |
| A61B 5/0245 | (2006.01) |
| A61B 5/352 | (2021.01) |

(52) U.S. Cl.
CPC ............ *A61B 5/36* (2021.01); *A61B 5/02455* (2013.01); *A61B 5/352* (2021.01); *A61B 5/7203* (2013.01)

(58) Field of Classification Search
CPC ........ A61B 5/346–366; A61B 5/02455; A61B 5/7203
See application file for complete search history.

(56) References Cited

U.S. PATENT DOCUMENTS

| | | |
|---|---|---|
| 2010/0056939 A1 | 3/2010 | Tarassenko et al. |
| 2010/0191133 A1 | 7/2010 | Hadley |
| 2011/0092838 A1 | 4/2011 | Helfenbein et al. |
| 2016/0135708 A1 | 5/2016 | Chakravarthy et al. |

OTHER PUBLICATIONS

International Search Report and Written Opinion, issued by the International Searching Authority (ISA/EP) in PCT Application No. PCT/FI2020/050099 dated Apr. 24, 2020. 10 pages.

(Continued)

*Primary Examiner* — Scott M. Getzow
(74) *Attorney, Agent, or Firm* — Meunier Carlin & Curfman LLC

(57) ABSTRACT

A method for QT correction is provided, the method comprising receiving an ECG signal; extracting a plurality of beat-to-beat (RR) intervals; extracting a plurality of QT intervals; computing a first probability distribution for a range of QT values based on the plurality of QT intervals; computing a second probability distribution for a range of QT values based on the plurality of QT intervals and the plurality of RR intervals; solving one or more points, wherein the first probability distribution and the second probability distribution intersect or wherein a difference between the first probability distribution and the second probability distribution is below a pre-defined difference threshold; designating one of one or more QT values corresponding to the one or more points as a corrected QT interval for a given QT interval of the plurality of QT intervals.

20 Claims, 6 Drawing Sheets

(56) References Cited

OTHER PUBLICATIONS

Written Opinion of the International Preliminary Examining Authority (IPEA/EP) issued in PCT Application No. PCT/FI2020/050099 dated Dec. 17, 2020. 6 pages.

International Preliminary Examination Report, issued by the International Preliminary Examining Authority (IPEA/EP) in PCT Application No. PCT/FI2020/050099 dated Mar. 22, 2021, 12 pages.

Potapov, Ilya, et al. Information transfer in QT-RR dynamics: Application to QT-correction. Scientific reports 8.1 (2018): 1-9.

The Clinical Evaluation of QT/QTc Interval Prolongation and Proarrhythmic Potential for Non-Antiarrhythmic Drugs, Announcement EMEA, EMEA GB No. CHMP/ICH/2/04, 2005, 1-14. XP007916110.

Goldenberg et al. QT interval: how to measure it and what is "normal". Journal of cardiovascular electrophysiology. 17.3 (2006): 333-336.

Jacquemet et al. Evaluation of a subject-specific transfer-function based nonlinear QT interval rate-correction method. Physiological Measurement 32(6), 2011, 619-635.

Helfenbein et al. An algorithm for continuous real-time QT interval monitoring. Journal of Electrocardiology 39(4), 2006, S123-S127.

Wong et al. Comparing Six QT Correction Methods in an Athlete Population. Computing in Cardiology 39, 2012, 585-588.

APPARATUS AND A METHOD FOR QT CORRECTION

PRIORITY

This application is a continuation application of international application PCT/FI2020/050099 filed on Feb. 18, 2020, which claims priority of Finnish patent application 20195214 filed on Mar. 22, 2019, the contents of both of which are incorporated herein by reference.

TECHNICAL FIELD

Various example embodiments relate to an apparatus and a method for QT correction of an electrocardiogram.

BACKGROUND

Electrocardiography is a process of recording electrical activity of the heart. Electrocardiogram (ECG) is a graph of voltage versus time produced by electrocardiography recording. The ECG signal has recognizable components, such as the P wave representing the depolarization of the atria of the heart, the QRS complex representing the depolarization of the ventricles of the heart, and the T wave representing the repolarization of the ventricles. The QT interval is calculated as the time from the start of the Q wave to the end of the T wave. Too short or too long QT times are associated with cardiac malfunction. However, the QT times vary with the heart rate (HR) and thus depend on the situation. For example, amounts of rest and exercise, and the level of anxiety may affect HR and thus also QT times. Therefore, the QT times are normalized for HR equal to 60 heart beats per minute (bpm). The normalization yields the so-called corrected QT time (QTc), which is a fundamental risk measure in cardiology.

The existing QT correction formulas, such as Bazett's formula and Fridericia's formula, are considered to be inaccurate, especially at high and/or low heart rates.

Therefore, there is a need for an improved solution for the QT correction.

SUMMARY

The problem mentioned above is alleviated by providing a method and technical equipment, where the method is implemented. Various aspects comprise a method, an apparatus, and a computer program product comprising a computer program stored therein, which are characterized by what is stated in the independent claims. Various example embodiments are disclosed in the dependent claims.

According to a first aspect, a method is provided, the method comprising receiving an ECG signal; extracting a plurality of beat-to-beat (RR) intervals; extracting a plurality of QT intervals; computing a first probability distribution for a range of QT values based on the plurality of QT intervals; computing a second probability distribution for a range of QT values based on the plurality of QT intervals and the plurality of RR intervals; solving one or more points, wherein the first probability distribution and the second probability distribution intersect or wherein a difference between the first probability distribution and the second probability distribution is below a pre-defined difference threshold; designating one of one or more QT values corresponding to the one or more solved points as a corrected QT interval for a given QT interval of the plurality of QT intervals.

According to an embodiment, the first probability distribution defines a probability of detecting the given QT interval of the plurality of QT intervals provided the QT interval(s) prior to the given QT interval were detected.

According to an embodiment, the second probability distribution defines a probability of detecting the given QT interval of the plurality of QT intervals provided the QT interval(s) prior to the given QT interval and the RR interval(s) prior to the given QT interval or a given RR interval of the plurality of RR intervals were detected.

According to an embodiment, the QT intervals prior to the given QT interval comprise 5 to 10 QT intervals preceding the given QT interval.

According to an embodiment, the RR intervals prior to the given RR interval comprise 5 to 10 RR intervals preceding the given RR interval.

According to an embodiment, the method further comprises designating the one or more QT values corresponding to the one or more solved points as one or more candidate QT intervals for the given QT interval; and selecting a candidate QT interval which is closest to a QT interval observed at a pre-defined heart rate to be designated as the corrected QT interval.

According to an embodiment, the method further comprises, in response to not observing the pre-defined heart rate, extrapolating QT and RR data derived from the ECG signal towards the pre-defined heart rate.

According to an embodiment, the method further comprises designating the one or more QT values corresponding to the one or more solved points as one or more candidate QT intervals for the given QT interval; and selecting a candidate QT interval which has a maximum probability to be designated as the corrected QT interval.

According to an embodiment, the method further comprises designating the one or more QT values corresponding to the one or more solved points as one or more candidate QT intervals for the given QT interval; and forming a relation based on at least a probability of a candidate QT interval, a distance between the QT candidate interval and a QT interval observed at a pre-defined heart rate, and a distance between the QT candidate interval and the given QT interval;

selecting a candidate QT interval minimizing the relation to be designated as the corrected QT interval.

According to an embodiment, the method further comprises one or more of: providing the corrected QT for display; providing results determined based on an electrocardiography recording for display; causing an alarm if the corrected QT interval is below a first pre-defined threshold or above a second pre-defined threshold.

According to a second aspect, an apparatus is provided, the apparatus comprising means for performing: receiving an ECG signal; extracting a plurality of beat-to-beat (RR) intervals; extracting a plurality of QT intervals; computing a first probability distribution for a range of QT values based on the plurality of QT intervals; computing a second probability distribution for a range of QT values based on the plurality of QT intervals and the plurality of RR intervals; solving one or more points, wherein the first probability distribution and the second probability distribution intersect or wherein a difference between the first probability distribution and the second probability distribution is below a pre-defined difference threshold; designating one of one or more QT values corresponding to the one or more solved points as a corrected QT interval for a given QT interval of the plurality of QT intervals.

According to an embodiment, the means comprises at least one processor; at least one memory including computer program code; the at least one memory and the computer program code configured to, with the at least one processor, cause the performance of the apparatus.

According to an embodiment, the apparatus is a wearable monitoring device or an electrocardiogram monitoring device.

According to a third aspect, a computer program is provided, comprising computer program code configured to, when executed on at least one processor, cause an apparatus to perform at least receiving an ECG signal; extracting a plurality of beat-to-beat (RR) intervals; extracting a plurality of QT intervals; computing a first probability distribution for a range of QT values based on the plurality of QT intervals; computing a second probability distribution for a range of QT values based on the plurality of QT intervals and the plurality of RR intervals; solving one or more points, wherein the first probability distribution and the second probability distribution intersect or wherein a difference between the first probability distribution and the second probability distribution is below a pre-defined difference threshold; designating one of one or more QT values corresponding to the one or more solved points as a corrected QT interval for a given QT interval of the plurality of QT intervals.

DESCRIPTION OF THE DRAWINGS

In the following, various example embodiments will be described in more detail with reference to the appended drawings, in which.

DESCRIPTION OF EXAMPLE EMBODIMENTS

Figure 1:
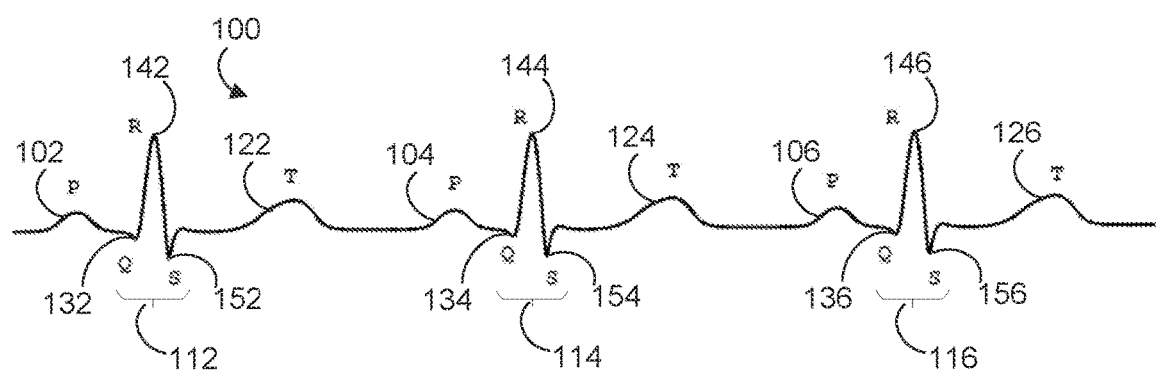
FIG. 1 shows, by way of example, an ECG signal.

FIG. 1 shows, by way of an example, an ECG signal 100. The ECG signal may be broken down into several components. P waves 102, 104, 106 represent the depolarization of the atria, QRS complexes 112, 114, 116 represent the depolarization of the ventricles, and T waves 122, 124, 126 represent the repolarization of the ventricles. Q waves 132, 134, 136 are downward deflections following the P waves. R waves 142, 144, 146, or R peaks, follow as upward deflections, and S waves 152, 154, 156 are downward deflections after the R waves.

Figure 2:
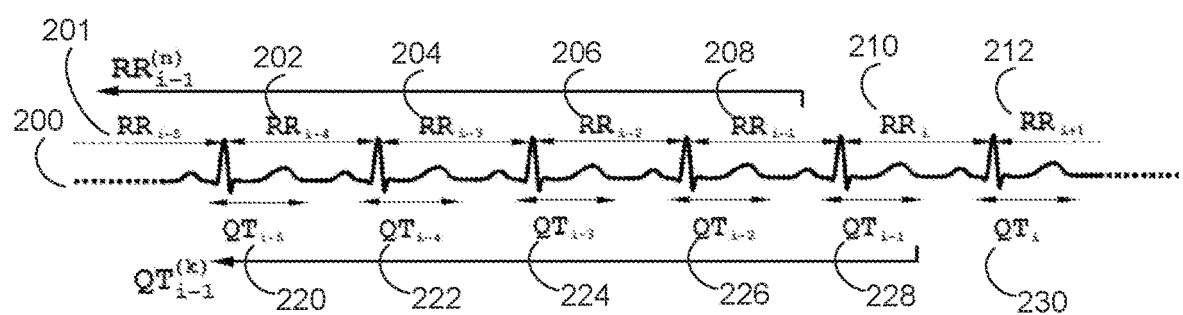
FIG. 2 shows, by way of example, RR intervals and QT intervals in an ECG signal.

FIG. 2 shows, by way of an example, RR intervals 202, 204, 206, 208, 210, 212 and QT intervals 220, 222, 224, 226, 228, 230 in an ECG signal 200. The RR interval is a beat-to-beat interval which is calculated as the time between successive R-peaks. The QT interval is calculated as the time from the start of the Q wave to the end of the T wave.

The QT intervals and RR intervals depend on the heart rate, which on the other hand depends on various factors such as age, gender, and/or physiological status of a person. Physiological status here may refer to rest, sleep, exercise, anxiety, etc. In order to assess duration of the QT interval universally among people and/or for different heart rates, QT intervals need to be corrected.

Figure 3:
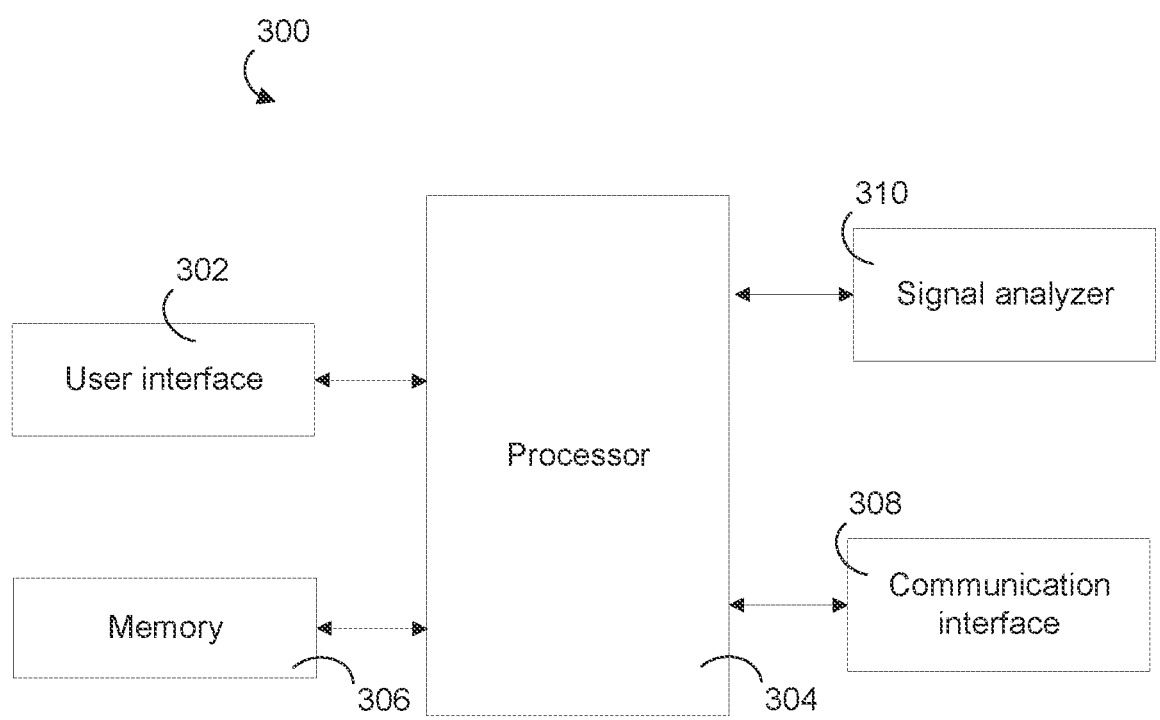
FIG. 3 shows, by way of example, a block diagram of an apparatus for QT correction.

FIG. 3 shows, by way of an example, a block diagram of an apparatus 300 for QT correction. The apparatus may be e.g. a server or a computer or a smart phone. Alternatively, the apparatus may be or may comprise an ECG monitoring device, such as a Holter machine or a large-scale ECG monitor. Alternatively, the apparatus may be a wearable monitoring device, e.g. a sport watch, smart ring or any wearable heart rate monitor capable of measuring a signal representing electrical activity of the heart of a user of the wearable monitoring device and determining QT intervals from the signal. The apparatus may receive user input such as commands, parameters etc. via a user interface 302 and/or via a communication interface 308. Examples of the commands comprise a command to reset an alarm. The user interface may receive user input e.g. through buttons and/or a touch screen. Alternatively, the user interface may receive user input from the Internet or a personal computer or a smartphone via a communication connection. The communication connection may be e.g. the Internet, a mobile communication network, Wireless Local Area Network (WLAN), Bluetooth®, or other contemporary and future networks. The apparatus may comprise a memory 306 for storing data and computer program code which may be executed by a processor 304 to carry out various embodiments of the method as disclosed herein. A signal analyzer 310 may be configured to implement the elements of the method disclosed herein. The signal analyzer may receive a signal to be processed, e.g. an ECG signal, from the memory or from the heart rate monitoring unit capable of measuring a signal representing electrical activity of the heart and determining QT intervals from the signal. The elements of the method may be implemented as a software component residing in the apparatus. The apparatus may receive the signal to be processed e.g. from a monitoring device and store the signal in the memory. The monitoring device may be any ECG hardware as described above. A computer program product may be embodied on a non-transitory computer readable medium. The apparatus may comprise means such as circuitry and electronics for handling, receiving and transmitting data, such as an ECG signal.

It should be appreciated that at least in some embodiments, the user interface 302 may alternatively or additionally provide output or displaying of information to a user of the apparatus. Examples of the user interface comprise one or more or a combination of a speaker, a display, a touch screen, light source and a printer. The information displayed by the user interface may comprise one or more from an alarm, an electrocardiogram, a QT value and a corrected QT interval. The alarm may be a visual alarm or an audio alarm or a combination thereof. Examples of audio alarms comprise sounds. Examples of visual alarms comprise graphical user interface elements for example symbols and light sources whose color may be set, e.g. red, to indicate an alarm.

It should be appreciated that the apparatus 300, for example an electrocardiogram monitoring device, may be further caused to display, by the user interface, one or more results determined based on an electrocardiography recording performed by the device, together with the corrected QT interval. In this way, the user of the apparatus may be assisted to correctly evaluate results of the electrocardiography recording and/or any alarm caused by the apparatus for continued interaction with the apparatus. The results of the electrocardiography recording may be displayed by the user interface. Examples of the results of the electrocardiography recording comprise or at least indicate: an electrocardiogram, a QT value, sinus rhythm, sinus tachycardia, sinus bradycardia, atrial fibrillation, atrial flutter, ventricular, tachycardia, ventricular fibrillation and/or heart rate. In an example, when the corrected QT interval is displayed with a QT value, the user may be assisted to correctly interpret the QT value based on the corrected QT interval. In another example, displaying the corrected QT interval may provide that the user may be assisted to interpret an alarm caused by the device and to determine to input a command to reset or not to reset the alarm such that continued use of the apparatus may be facilitated.

Figure 4:
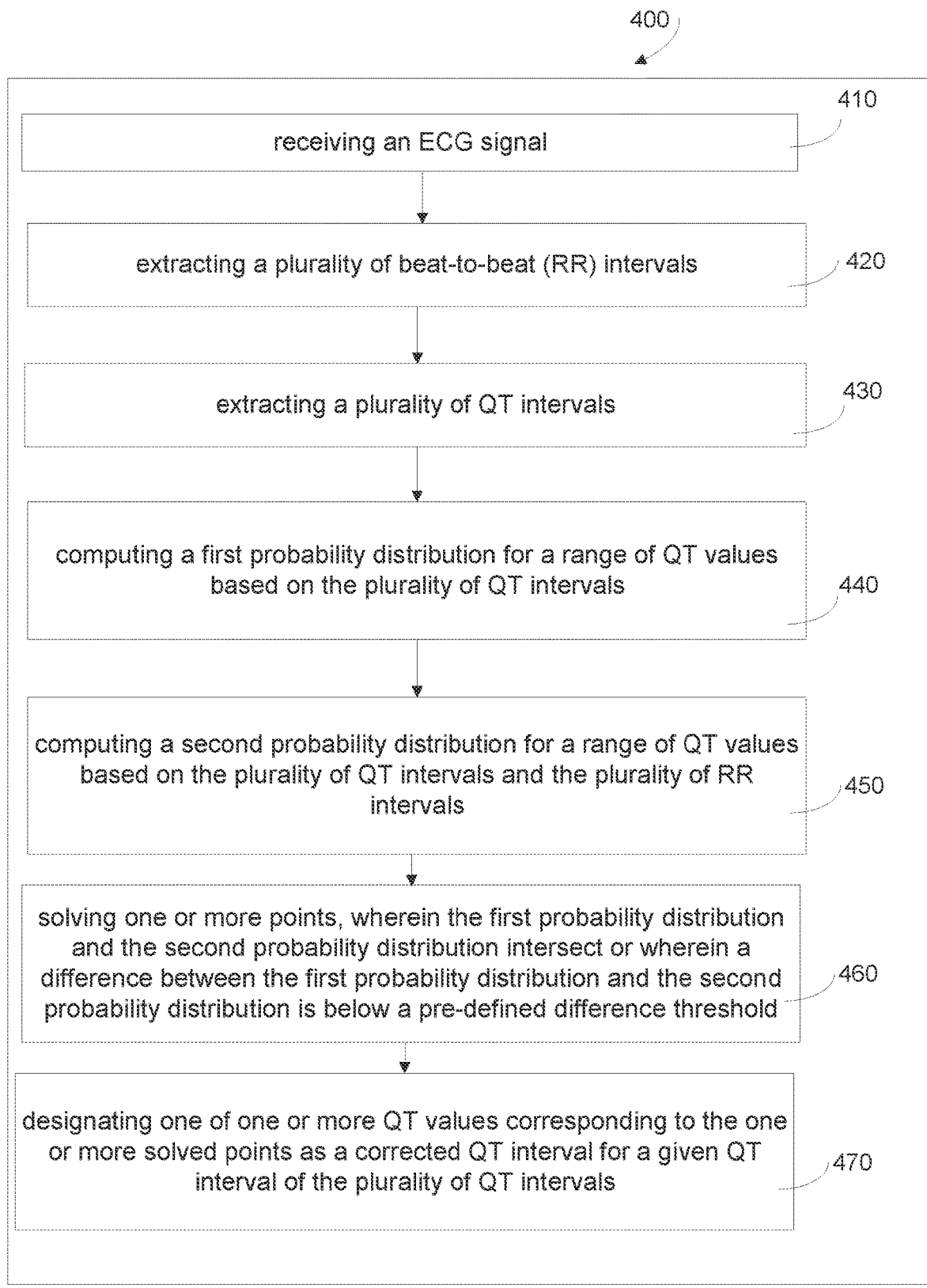
FIG. 4 shows, by way of example, a flowchart of a method for QT correction.

There is provided a method for QT correction. FIG. 4 shows, by way of an example, a flowchart of a method 400 for QT correction. The method comprises receiving 410 an ECG signal. The method comprises extracting 420 a plurality of beat-to-beat (RR) intervals. The method comprises extracting 430 a plurality of QT intervals. The method comprises computing 440 a first probability distribution for a range of QT values based on the plurality of QT intervals. The method comprises computing 450 a second probability distribution for a range of QT values based on the plurality of QT intervals and the plurality of RR intervals. The method comprises solving 460 one or more points, wherein the first probability distribution and the second probability distribution intersect or wherein a difference between the first probability distribution and the second probability distribution is below a pre-defined difference threshold. The method comprises designating 470 one of one or more QT values corresponding to the one or more solved points as a corrected QT interval for a given QT interval of the plurality of QT intervals.

In an example, the solved points are intersection points, wherein the first probability distribution is substantially equal or equal to the second probability distribution.

Alternatively, the solved points are points, wherein a difference between the first probability distribution and the second probability distribution is below a pre-defined difference threshold, as described later.

The transfer entropy method may be used to quantify information transfer between two related processes. Transfer entropy estimates information transfer, defined in Shannon terms, from a source process to a destination process. For example, transfer entropy may be used to estimate the amount of information transferred from the time dependent series of the RR intervals to that of the QT intervals. The estimation of the unidirectional transfer, RR-to-QT, is related to the amount of influence of the RR intervals exerted on the QT intervals. Thus, the RR-to-QT transfer quantifies the QT interval dependence on the RR intervals. If the transfer is equal to zero, the QT dependency on the RR intervals is removed.

The method 400 enables the removal of the QT dependency on the RR intervals and, hence, reliable determination of the corrected QT intervals for different heart rates. The estimation of the first probability distribution and the second probability distribution for a range of QT interval values enables determination of corrected QT interval(s) by finding candidate QT values where the first and the second probability distribution functions intersect or where a difference between the first probability distribution and the second probability distribution is below a pre-defined difference threshold. The method 400 enables correcting QT intervals by reducing to zero the information transfer from the RR intervals of ECG to the QT intervals synchronized in time.

The method 400 enables determination of the corrected QT intervals without using conventional formulas, such as Bazett's formula or Fridericia's formula which are considered inaccurate, especially at high and/or low heart rates.

The transfer entropy for the RR-to-QT transfer is defined by $$TE_{RR \to QT} = \sum p(QT_i, QT_{i-1}^{(k)}, RR_{i-1}^{(n)}) \times \log_2 \frac{p(QT_i | QT_{i-1}^{(k)}, RR_{i-n}^{(n)})}{p(QT_i | QT_{i-1}^{(k)})}$$

$QT_i$ is the i-th QT interval value in the time series. $RR_i$ is the i-th RR interval value corresponding to $QT_i$ in the time series. $QT_{i-1}^{(k)}$ are the QT interval values for k preceding heartbeats, i.e. beats prior to and not including the beat i. The QT values for the preceding beats are illustrated in FIG. 2 as $QT_{i-1}, QT_{i-2}, QT_{i-3}, QT_{i-4}, QT_{i-5}, \ldots, QT_{i-k}$. $RR_{i-1}^{(n)}$ are the RR interval values for the n preceding beats, i.e. beats prior to and not including the beat i. The RR values for the preceding beats are illustrated in FIG. 2 as $RR_{i-1}, RR_{i-2}, RR_{i-3}, RR_{i-4}, RR_{i-5}, \ldots, RR_{i-n}$. Traditionally, $RR_i$ is assumed to be an inter-beat interval before the corresponding $QT_i$, as shown in FIG. 2. $RR_{i+1}$ is the RR interval following the beat i.

Probability $p(QT_i/QT_{i-1}^{(k)})$ is a probability of observing, or detecting, $QT_i$ value provided the history $QT_{i-1}^{(k)}$ was observed, or detected. Probability $p(QT_i/QT_{i-1}^{(k)}, RR_{i-1}^{(n)})$ is a probability of observing, or detecting, $QT_i$ value provided both the history $QT_{i-1}^{(k)}$ and $RR_{i-1}^{(n)}$ were observed, or detected.

The method comprises computing the first probability distribution for a range of QT values based on the plurality of QT intervals. The first probability distribution defines the probability $p(QT_i/QT_{i-1}^{(k)})$. According to an embodiment, the first probability distribution defines a probability of detecting a given QT interval ($QT_i$) of the plurality of QT intervals provided QT intervals ($QT_{i-1}^{(k)}$) prior to the given QT interval were detected. The given QT interval may be the $QT_i$ 230. The QT intervals prior to the given QT interval may be a pre-defined number (k) of $QT_{i-1}$ 228, $QT_{i-2}$ 226, $QT_{i-3}$ 224, $QT_{i-4}$ 222, $QT_{i-5}$ 220, . . . , $QT_{i-k}$.

The method comprises computing the second probability distribution for a range of QT values based on the plurality of QT intervals and the plurality of RR intervals. The second probability distribution is $p(QT_i/QT_{i-1}^{(k)}, RR_{i-1}^{(n)})$. According to an embodiment, the second probability distribution defines a probability of detecting a given QT interval ($QT_i$) of the plurality of QT intervals provided the QT intervals ($QT_{i-1}^{(k)}$) prior to the given QT interval and the RR intervals ($RR_{i-1}^{(n)}$) prior to the given QT interval or the given RR interval ($RR_i$) of the plurality of RR intervals were detected. The given QT interval may be the $QT_i$ 230. The QT intervals prior to the given QT interval may be a pre-defined number (k) of $QT_{i-1}$ 228, $QT_{i-2}$ 226, $QT_{i-3}$ 224, $QT_{i-4}$ 222, $QT_{i-5}$ 220 . . . , $QT_{i-k}$. The given RR interval may be the $RR_i$ 210. The RR intervals prior to the given RR interval may be a pre-defined number (n) of $RR_{i-1}$ 208, $RR_{i-2}$ 206, $RR_{i-3}$ 204, $RR_{i-4}$ 202, $RR_{i-5}$ 201, . . . , $RR_{i-n}$.

The probabilities defined by the first probability distribution and the second probability distribution may be estimated by applying Kernel Density Estimation techniques. The kernel applied may be e.g. Gaussian kernel, box kernel or triangle kernel, or any suitable kernel. A kernel may be plotted around each point i with a width parameter estimated using e.g. the Silverman's rule or the Scott's rule when Gaussian kernel is applied. Alternatively, the width can be estimated by iteratively fitting kernels with a number of widths to a dataset and then selecting the best width. The kernel curves plotted around data points are summed up to get an estimation of the probability distribution.

The method comprises solving one or more points, wherein the first probability distribution and the second probability distribution intersect or wherein a difference between the first probability distribution and the second probability distribution is below a pre-defined difference threshold. When the first probability distribution equals, or substantially equals, or is close enough to the second probability distribution, the transfer entropy is substantially equal to zero and the QT dependency on the RR intervals is removed. Solving the one or more points, wherein the first probability distribution and the second probability distribution intersect or wherein a difference between the first probability distribution and the second probability distribution is below a pre-defined difference threshold, enables determination of the corrected QT interval(s).

Figure 5:
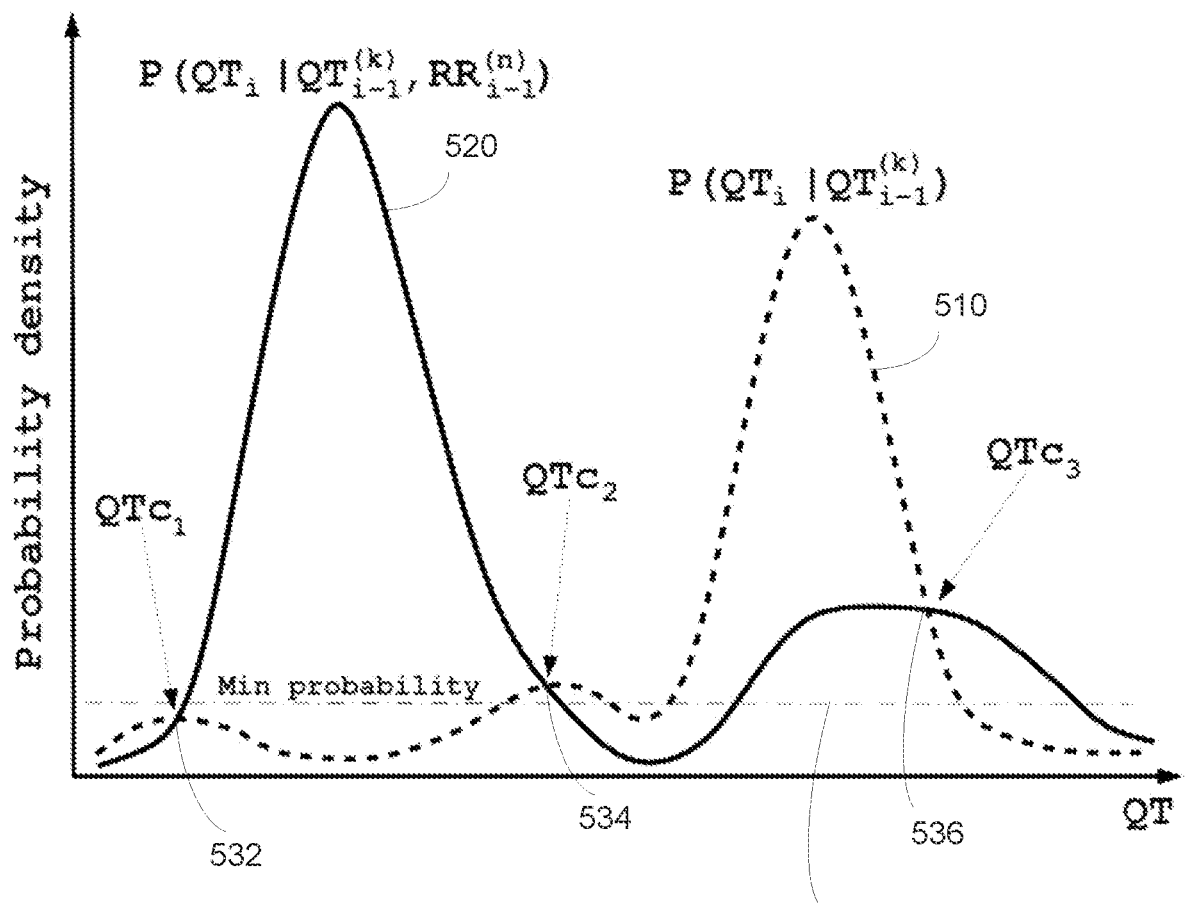
FIG. 5 shows, by way of example, probability distributions for a range of QT values.

FIG. 5 shows, by way of an example, probability distributions 510, 520 for a range of QT values. The first probability distribution 510 is illustrated with a dashed line. The second probability distribution 520 is illustrated with a solid line. The intersection points 532, 534, 536 of the probability distributions 510, 520 may be solved e.g. graphically or algebraically.

The intersection points indicate QT values that are independent from RR. The QT values QTc1, QTc2, QTc3 corresponding to the intersection points 532, 534, 536, respectively, may be designated as the candidate QT intervals. One of the candidate QT intervals may be designated as a corrected QT interval for the QT interval i.

There are alternative ways to select a candidate QT interval to be designated as the corrected QT interval.

For example, a candidate QT interval which is closest to the QT interval observed at a pre-defined heart rate HR0 may be selected to be designated as the corrected QT interval. Commonly HR0 corresponds to the heart rate at rest with references to 60 bpm being often used by medical personnel. The heart rate of 60 bpm corresponds to the RR interval of 1000 ms. A candidate QT interval which is closest to the QT interval observed at the heart rate of 60 bpm or at the RR interval of 1000 ms may be selected to be designated as the corrected QT interval. This method may be called a proximity method. Let us designate the QT interval observed at HR0 as QT0. It is to be understood, that any pre-defined heart rate may be used for normalization.

In case HR0 is not observed in the measured data, HR0 may be estimated using extrapolation. For example, polynomial extrapolation may be used to extrapolate data towards the pre-defined heart rate HR0, such as 60 bpm or to the RR interval of 1000 ms, to find QT0. For example, polynomial extrapolation with degree of 2 may be applied. Relationship between QT and RR is biphasic and therefore the degree of 2 is suitable to be used in the extrapolation. However, any other suitable extrapolation may be used.

As another example, a candidate QT interval which has a maximum probability may be selected to be designated as the corrected QT interval. In the example of FIG. 5, $QTc_3$ denotes the intersection point wherein the QT value has the highest probability compared to the QT values at the intersection points $QTc_1$ and $QTc_2$. Selection of the candidate QT interval based on the maximum probability is justified by having this value occurring more often.

As another example, the corrected QT interval may be selected using a compound relation, combining contributions from many factors, such as QT0 proximity ($\Delta_{QT0}$), probability of a candidate QT ($P_{QTc}$), correction distance ($\Delta_{QT}$, see below), and others. Note that in this approach other factors can be found as to be included into the relation. In this case, the corrected QT interval is the one maximizing the overall positive contribution of all these factors. For instance, the corrected QT interval may be found as (other relations can be devised too):

$$QTc = \underset{QTc_k}{\operatorname{argmin}}\left(\frac{C \cdot \Delta_{QT0}(QTc_k) - \Delta_{QT}(QTc_k)}{P_{QTc}(QTc_k)}\right)$$

where C is a constant factor, $\Delta_{QT0}(QTc_k)=|QTc_k-QT0|$, $\Delta_{QT}(QTc_k)=|QTc_k-QT_i|$, and $P_{QTc}(QTc_k)$ is the probability of a candidate QT interval $QTc_k$. The user is free to determine the contribution weight of the QT0-proximity $\Delta_{QT0}$ as a fraction of the correction distance $\Delta_{QT}$ by varying the constant C, which can assume any non-negative value. By minimizing the proposed relation, one finds $QTc_k$ that balance individual contributions from the three factors: namely, minimizing $\Delta_{QT0}$ and maximizing $\Delta_{QT}$ and $P_{QTc}$.

A minimum probability 540, as shown in FIG. 5, may be pre-determined as the minimum threshold beyond which the QTc value should be sought. In other words, too low probabilities may be rejected as improbable. In the example of FIG. 5, QTc1 is rejected if the minimum probability threshold is pre-determined. Determination of the minimum probability improves the accuracy and reliability of the determination of the corrected QT intervals.

As described above, a difference threshold may be applied in solving the points. Namely, if two probability density functions 510, 520 come close enough to each other wherein the difference between the functions is below the threshold, this point may be considered as an intersection point. An intersection point of the first probability distribution and the second probability distribution may be determined on the basis of the first probability distribution being equal or substantially equal, or close enough to, the second probability distribution. This covers the situation, wherein a difference between the first probability distribution and the second probability distribution is below a difference threshold. The difference threshold may be pre-defined e.g. by the user and expressed in fraction of the maximum observed probability of the first and/or second probability distributions. Thresholds of 5, 10, or 15% are examples of the fraction of the maximum observed probability. When applying the difference threshold in determination of intersection points, more intersections points, and thus more candidate values, may be found. Hence, errors in the probability distribution estimation are mitigated by allowing more variability in the QTc candidate values.

According to an embodiment, the QT intervals prior to the given $QT_i$ interval comprise 5 to 10 QT intervals preceding the given $QT_i$ interval. In other words, a value for k, i.e. number of the preceding QT intervals, may be e.g. 5 to 10. The value for k may, however, be more or less than 10, e.g. 1, 2, 3, 4, 11, 12, 13, 14, 15 etc. The more preceding QT intervals are taken into account in the probability calculation, the more accurate the correction may be. However, after certain number of preceding QT intervals, the accuracy does not significantly change anymore due to the limitations of the finite size of the data.

According to an embodiment, the RR intervals prior to the given $RR_i$ interval comprise 5 to 10 RR intervals preceding the given $RR_i$ interval. In other words, a value for n, i.e. number of the preceding RR intervals may be e.g. 5 to 10.

The value for n may, however, be more or less than 10, e.g. 1, 2, 3, 4, 11, 12, 13, 14, 15 etc. The more preceding RR intervals are taken into account in the probability calculation, the more accurate the correction may be. However, after certain number of preceding RR intervals, the accuracy does not significantly change anymore due to the limitations of the finite size of the data.

Value for n may be different than the value for k.

Figure 6:
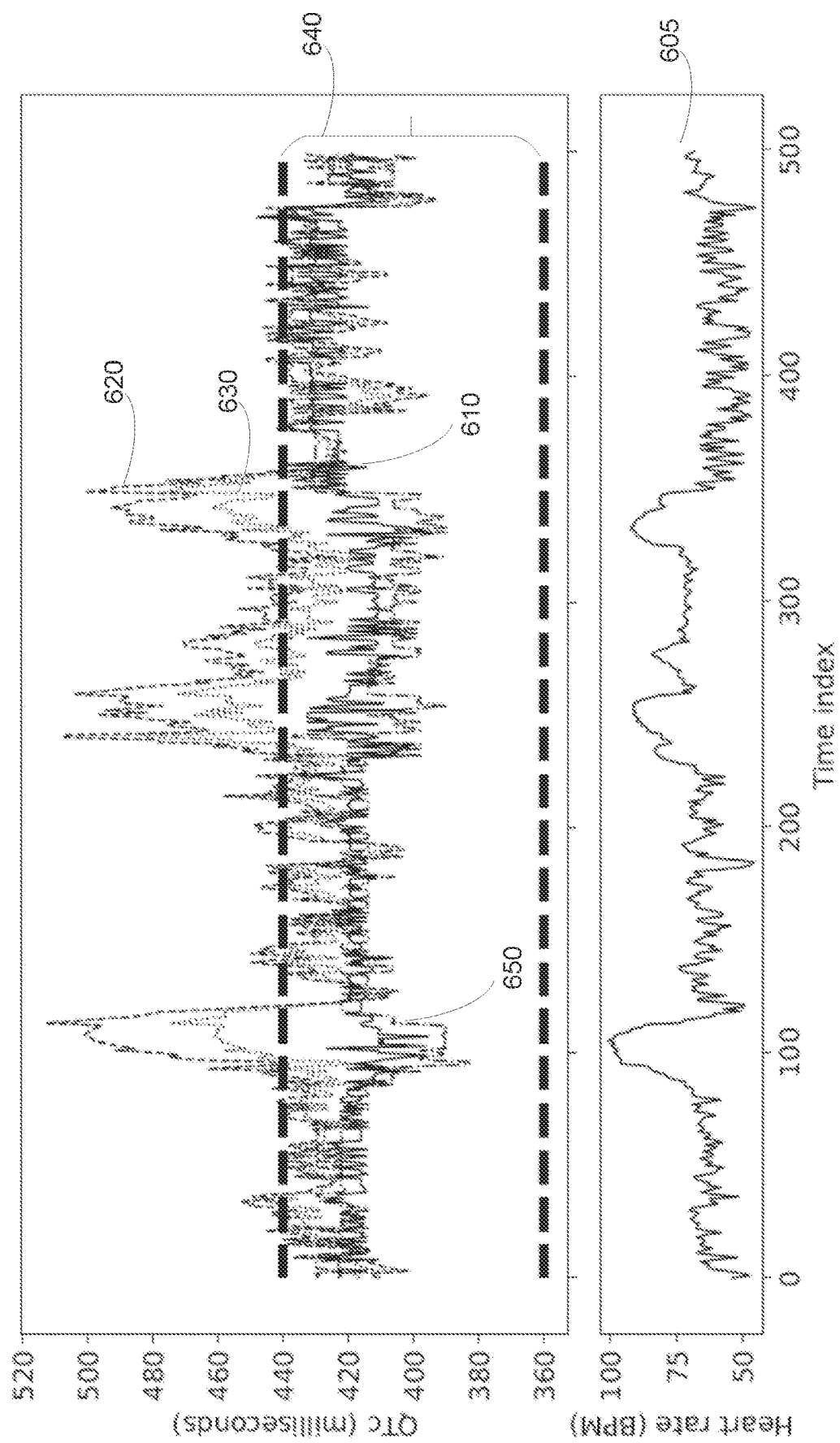
FIG. 6 shows, by way of example, a result of QT correction.

FIG. 6 shows, by way of an example, a result of QT correction. In this example, an ECG of a healthy subject has been measured. Subsequently, the QT and RR interval time series were extracted from the ECG. The dashdotted line 650 represents the raw, uncorrected QT intervals. The solid line 610 represents corrected QT intervals resulting from the method disclosed herein. The dashed line 620 represents corrected QT intervals by the Bazett's method. The dotted line 630 represents corrected QT intervals by the Fridericia's method. The QT range 640 represents the normal range of the corrected QT for a healthy subject. Thus, as can be seen in FIG. 6, the Bazett's method and the Fridericia's method tend to overestimate the QT values. The most challenging regions for QT correction are those with high or varying heart rates, as shown by the heart rate signal 605. The time indexes of the QT signals 610, 620, 630 correspond to the time indexes of the heart rate signal 605. Finally, the QT corrected line 610 has a characteristic flatness confirming independence of the corrected QT from the RR intervals.

Figure 7:
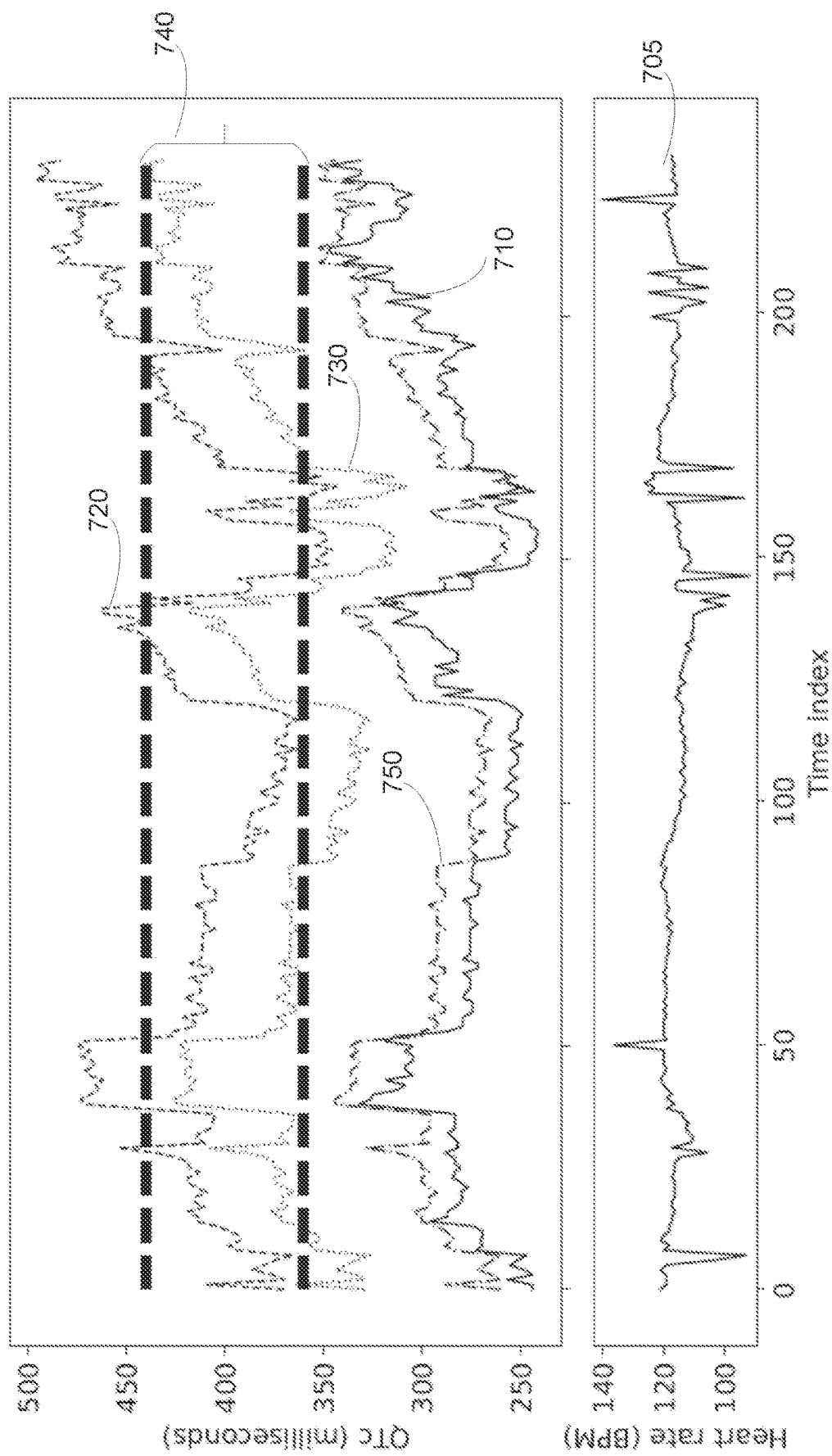
FIG. 7 shows, by way of example, a result of QT correction.

FIG. 7 shows, by way of an example, a result of QT correction. In this example, an ECG of a subject with a pathology leading to shortening of the QT interval has been measured. The dashdotted line 750 represents the raw, uncorrected QT intervals. The solid line 710 represents corrected QT intervals resulting from the method disclosed herein. The dashed line 720 represents corrected QT intervals by the Bazett's method. The dotted line 730 represents corrected QT intervals by the Fridericia's method. The QT range 740 represents the normal range of the corrected QT for a healthy subject. Thus, as can be seen in the FIG. 7, the Bazett's method and the Fridericia's method tend to overestimate the QT values and the harmful condition of the subject with the short QT is not detected. The corrected QT shown by the solid line 710 correctly shows QT intervals that are not in the normal range 740 but are shorter than normal. The signal 705 represents the heart rate signal. The time indexes of the QT signals 710, 720, 730 correspond to the time indexes of the heart rate signal 705.

Corrected QT may be e.g. displayed to the user on a user interface, for example a display, of an apparatus. In the case of the abnormal corrected QT intervals an alarming signal may be utilized to attract attention of the user. Since the apparatus reported herein estimated the corrected QT for each heartbeat, the average corrected QT or other summary may be presented to the user to increase practical effect. QT time representing the repolarization time of the heart is rate dependent and if the corrected QT time exceeds certain limit, which depends on the gender and mutation, the individual is at increased risk of having a potentially lethal arrhythmia. Thus, also in the clinical use, QT time has to be adjusted to obtain the correct QT value to detect whether the individual is at increased arrhythmia risk. Corrected QT may, thus, be used to evaluate whether the repolarization time of the heart of an individual is normal and to detect possible diseases affecting repolarization time e.g. a long QT syndrome or a short QT syndrome. Abnormal serum electrolyte levels, e.g. potassium concentration, also affect the repolarization time and those could be observed with ECG recording and corrected QT analysis. Additionally, some drugs, which are already on the market, prolong repolarization time of the heart in some individuals and it is clinically important to detect the correct QT interval of those situations and avoid those medications in those vulnerable patients.

An apparatus may comprise at least one processor, at least one memory including computer program code, and the at least one memory and the computer program code may be configured to, with the at least one processor, cause the apparatus to perform: receiving an ECG signal; extracting a plurality of beat-to-beat (RR) intervals; extracting a plurality of QT intervals; computing a first probability distribution for a range of QT values based on the plurality of QT intervals; computing a second probability distribution for a range of QT values based on the plurality of QT intervals and the plurality of RR intervals; solving one or more points, wherein the first probability distribution and the second probability distribution intersect or wherein a difference between the first probability distribution and the second probability distribution is below a pre-defined difference threshold; designating one of one or more QT values corresponding to the one or more points as a corrected QT interval for a given QT interval of the plurality of QT intervals.

The apparatus may be configured to perform: designating the one or more QT values corresponding to the one or more intersection points as one or more candidate QT intervals for the given QT interval; and selecting a candidate QT interval which is closest to a QT interval observed at a pre-defined heart rate to be designated as the corrected QT interval.

The apparatus may be configured to perform, in response to not observing the pre-defined heart rate, extrapolating QT and RR data derived from the ECG signal towards the pre-defined heart rate.

The apparatus may be configured to perform designating the one or more QT values corresponding to the one or more intersection points as one or more candidate QT intervals for the given QT interval; and selecting a candidate QT interval which has a maximum probability to be designated as the corrected QT interval.

The apparatus may be configured to perform designating the one or more QT values corresponding to the one or more intersection points as one or more candidate QT intervals for the given QT interval; and forming a relation based on at least a probability of a candidate QT interval, a distance between the QT candidate interval and a QT interval observed at a pre-defined heart rate, and a distance between the QT candidate interval and the given QT interval; selecting a candidate QT interval minimizing the relation to be designated as the corrected QT interval.

The apparatus may be configured to perform one or more of: providing the corrected QT interval for display; providing results determined based on an electrocardiography recording for display; causing an alarm if the corrected QT interval is below a first pre-defined threshold or above a second pre-defined threshold.

It is obvious that the present invention is not limited solely to the above-presented embodiments, but it can be modified within the scope of the appended claims.

Embodiments described herein are industrially applicable at least in monitoring electrical activity of the heart.

What is claimed is:

1. A method comprising
receiving, by an apparatus, an electrocardiogram, ECG, signal;
extracting, by the apparatus, a plurality of beat-to-beat (RR) intervals;
extracting a plurality of QT intervals;

computing, by the apparatus, a first probability distribution for a range of QT values based on the plurality of QT intervals;
computing, by the apparatus, a second probability distribution for a range of QT values based on the plurality of QT intervals and the plurality of RR intervals;
solving, by the apparatus, one or more points, wherein the first probability distribution and the second probability distribution intersect or wherein a difference between the first probability distribution and the second probability distribution is below a pre-defined difference threshold;
designating, by the apparatus, one of one or more QT values corresponding to the one or more solved points as a corrected QT interval for a given QT interval of the plurality of QT intervals.

2. The method according to claim 1,
wherein the first probability distribution defines a probability of detecting the given QT interval of the plurality of QT intervals provided the QT interval(s) prior to the given QT interval were detected.

3. The method according to claim 1,
wherein the second probability distribution defines a probability of detecting the given QT interval of the plurality of QT intervals provided the QT interval(s) prior to the given QT interval and the RR interval(s) prior to the given QT interval or a given RR interval of the plurality of RR intervals were detected.

4. The method according to claim 2, wherein the QT intervals prior to the given QT interval comprise 5 to 10 QT intervals preceding the given QT interval.

5. The method according to claim 3, wherein the RR intervals prior to the given RR interval comprise 5 to 10 RR intervals preceding the given RR interval.

6. The method according to claim 1, further comprising
designating the one or more QT values corresponding to the one or more solved points as one or more candidate QT intervals for the given QT interval; and
selecting a candidate QT interval which is closest to a QT interval observed at a pre-defined heart rate to be designated as the corrected QT interval.

7. The method according to claim 6, further comprising
in response to not observing the pre-defined heart rate, extrapolating QT and RR data derived from the ECG signal towards the pre-defined heart rate.

8. The method according to claim 1, further comprising
designating the one or more QT values corresponding to the one or more solved points as one or more candidate QT intervals for the given QT interval; and
selecting a candidate QT interval which has a maximum probability to be designated as the corrected QT interval.

9. The method according to claim 1, further comprising
designating the one or more QT values corresponding to the one or more solved points as one or more candidate QT intervals for the given QT interval; and
forming a relation based on at least a probability of a candidate QT interval, a distance between the QT candidate interval and a QT interval observed at a pre-defined heart rate, and a distance between the QT candidate interval and the given QT interval;
selecting a candidate QT interval minimizing the relation to be designated as the corrected QT interval.

10. The method according to claim 1, further comprising one or more of:
providing the corrected QT interval for display;
providing results determined based on an electrocardiography recording for display;
causing an alarm if the corrected QT interval is below a first pre-defined threshold or above a second pre-defined threshold.

11. An apparatus comprising means for performing:
receiving an ECG signal;
extracting a plurality of beat-to-beat (RR) intervals;
extracting a plurality of QT intervals;
computing a first probability distribution for a range of QT values based on the plurality of QT intervals;
computing a second probability distribution for a range of QT values based on the plurality of QT intervals and the plurality of RR intervals;
solving one or more points, wherein the first probability distribution and the second probability distribution intersect or wherein a difference between the first probability distribution and the second probability distribution is below a pre-defined difference threshold;
designating one of one or more QT values corresponding to the one or more solved points as a corrected QT interval for a given QT interval of the plurality of QT intervals.

12. The apparatus according to claim 11, wherein the first probability distribution defines a probability of detecting the given QT interval of the plurality of QT intervals provided the QT interval(s) prior to the given QT interval were detected.

13. The apparatus according to claim 11, wherein the means are further configured to perform:
designating the one or more QT values corresponding to the one or more solved points as one or more candidate QT intervals for the given QT interval; and
selecting a candidate QT interval which is closest to a QT interval observed at a pre-defined heart rate to be designated as the corrected QT interval.

14. The apparatus according to claim 11, wherein the means are further configured to perform:
in response to not observing the pre-defined heart rate, extrapolating QT and RR data derived from the ECG signal towards the pre-defined heart rate.

15. The apparatus according to claim 11, wherein the means are further configured to perform:
designating the one or more QT values corresponding to the one or more solved points as one or more candidate QT intervals for the given QT interval; and
selecting a candidate QT interval which has a maximum probability to be designated as the corrected QT interval.

16. The apparatus according to claim 11, wherein the means are further configured to perform:
designating the one or more QT values corresponding to the one or more solved points as one or more candidate QT intervals for the given QT interval; and
forming a relation based on at least a probability of a candidate QT interval, a distance between the QT candidate interval and a QT interval observed at a pre-defined heart rate, and a distance between the QT candidate interval and the given QT interval;
selecting a candidate QT interval minimizing the relation to be designated as the corrected QT interval.

17. The apparatus according to claim 11, wherein the means are further configured to perform:
providing the corrected QT interval for display;
providing results determined based on an electrocardiography recording for display;

causing an alarm if the corrected QT interval is below a first pre-defined threshold or above a second pre-defined threshold.

18. The apparatus according to claim 11, wherein the means comprises at least one processor; at least one memory including computer program code; the at least one memory and the computer program code configured to, with the at least one processor, cause the performance of the apparatus.

19. The apparatus according to claim 11, wherein the apparatus is a wearable monitoring device or an electrocardiogram monitoring device.

20. A non-transitory computer readable medium comprising computer program code configured to, when executed on at least one processor of an apparatus, cause the apparatus to perform:
- receiving an ECG signal;
- extracting a plurality of beat-to-beat (RR) intervals;
- extracting a plurality of QT intervals;
- computing a first probability distribution for a range of QT values based on the plurality of QT intervals;
- computing a second probability distribution for a range of QT values based on the plurality of QT intervals and the plurality of RR intervals;
- solving one or more points, wherein the first probability distribution and the second probability distribution intersect or wherein a difference between the first probability distribution and the second probability distribution is below a pre-defined difference threshold;
- designating one of one or more QT values corresponding to the one or more solved points as a corrected QT interval for a given QT interval of the plurality of QT intervals.

* * * * *